United States Patent
Ginggen

(10) Patent No.: US 7,637,897 B2
(45) Date of Patent: Dec. 29, 2009

(54) IMPLANTABLE PUMP WITH INTEGRATED REFILL DETECTION

(75) Inventor: Alec Ginggen, Neuchâtel (CH)

(73) Assignee: Codman Neuro Sciences Sarl, Le Locle (CH)

( * ) Notice: Subject to any disclaimer, the term of this patent is extended or adjusted under 35 U.S.C. 154(b) by 115 days.

(21) Appl. No.: 10/972,980

(22) Filed: Oct. 25, 2004

(65) Prior Publication Data

US 2006/0089619 A1    Apr. 27, 2006

(51) Int. Cl.
  *A61M 37/00* (2006.01)
(52) U.S. Cl. .................................. 604/288.01
(58) Field of Classification Search ...............................
  604/288.01–288.04, 260, 891.1, 116, 117, 604/890.1
  See application file for complete search history.

(56) References Cited

U.S. PATENT DOCUMENTS

| | | | |
|---|---|---|---|
| 4,013,074 A | 3/1977 | Siposs | |
| 4,557,722 A | 12/1985 | Harris | |
| 4,573,994 A | 3/1986 | Fischell et al. | |
| 4,760,837 A | 8/1988 | Petit | |
| 4,781,685 A | 11/1988 | Lehmann et al. | |
| 4,804,054 A | 2/1989 | Howson et al. | |
| 4,832,054 A | 5/1989 | Bark | |
| 5,006,115 A | 4/1991 | McDonald | |
| 5,009,644 A * | 4/1991 | McDonald | 604/175 |
| 5,171,228 A | 12/1992 | McDonald | |
| 5,527,307 A | 6/1996 | Srisathapat et al. | |
| 5,637,088 A | 6/1997 | Wenner et al. | |
| 5,707,361 A * | 1/1998 | Slettenmark | 604/131 |
| 5,836,915 A | 11/1998 | Steinbach et al. | |
| 5,957,890 A * | 9/1999 | Mann et al. | 604/131 |
| 6,577,899 B2 | 6/2003 | Lebel et al. | |
| 6,669,669 B2 * | 12/2003 | Flaherty et al. | 604/132 |
| 6,740,075 B2 | 5/2004 | Lebel et al. | |
| 6,755,814 B2 | 6/2004 | Wieland et al. | |
| 6,962,580 B2 * | 11/2005 | Adams et al. | 604/891.1 |
| 2007/0078381 A1 * | 4/2007 | Yap et al. | 604/65 |

FOREIGN PATENT DOCUMENTS

| | | |
|---|---|---|
| EP | 0 678 302 | 10/1995 |
| FR | 2 717 084 | 9/1995 |
| WO | WO 00/04944 | 2/2000 |

OTHER PUBLICATIONS

Partial European Search Report, from corresponding EP Appl. No. 05256581.9; mailed Feb. 17, 2006.

* cited by examiner

*Primary Examiner*—Kevin C Sirmons
*Assistant Examiner*—Elizabeth R Moulton
(74) *Attorney, Agent, or Firm*—Nutter McClennen & Fish LLP

(57) ABSTRACT

A refill port for an implantable device with integral refill instrument placement detection includes a pierceable septum and a detector. The pierceable septum is disposed on the refill port for admitting a refill instrument has a first outer surface at least a portion of which is exposed outside the refill port and a second inner surface at least a portion of which is exposed inside the refill port. The detector is disposed inside the refill port with respect to the second inner surface of the pierceable septum for determining the placement of a refill instrument within the refill port. The refill port can be provided on a refillable implantable drug delivery pump having control electronics so that the detector can trigger pump test features of the control electronics upon placement or removal of a refill instrument from the port.

28 Claims, 4 Drawing Sheets

Section A-A

Section B-B

Section C-C

Section D-D

Section E-E

IMPLANTABLE PUMP WITH INTEGRATED REFILL DETECTION

FIELD OF THE INVENTION

The invention relates generally to needle placement detecting devices, and in particular to needle placement detecting devices used in conjunction with a refillable medication dispensing apparatus.

BACKGROUND OF THE INVENTION

Various types of implantable medical devices, often referred to as implantable infusion pumps, are used for dispensing controlled volumes of a drug within a patient's body. These devices generally have reservoirs which are filled with a drug for dispensation at a dosage over time that is preprogrammed or programmable. Over time, as the drug is dispensed, the reservoir volume becomes depleted and needs to be refilled. Very often, the reservoir for receiving the drug has a refill port that is sealed with a self-sealing septum. To refill the reservoir, a doctor determines the location of the refill port by palpation of the patient's skin as the refill port typically protrudes from the infusion pump. The doctor the inserts a hypodermic needle through the skin and through the septum into the refill port. Once the needle is within the refill port, the medication is dispensed from a syringe into the refill port where it can refill the reservoir.

It is important to the performance of this process that the needle tip be properly positioned at the desired dispensing location. If the needle is not properly positioned within the refill port, medication can be improperly dispensed into the patient's body. The syringe can include, for example, a full month's worth of medication. It should be self evident that releasing such an amount of medication into the patient is likely to be detrimental.

It is also important to the performance of the refill process that pressures generated as a result of the refill not exceed the capability of the implantable infusion pump to contain the drug. For example, pressure generated in the delivery syringe, and thus at the end of the needle, can easily reach 5 to 10 bars. Such a high pressure level can potentially damage the delivery mechanism of the drug delivery device, often constituting a miniature valve, leading to a release of drug into the patient during the high-pressure episode.

One example of a prior art approach to determining whether a refill needle is properly placed is U.S. Pat. No. 5,171,288 to MacDonald. This patent describes a mechanism that detects the position of a needle based on a resonant circuit that is in an open-circuit state when the needle is not inserted into the refill port. The resonant circuit is closed when the needle is inserted into the port by a flow of electrical charge through the needle, the contact between the needle and the medical device, and body tissues that close the loop from the medical device back to the needle. Problems with this approach include the necessity of transmitting energy even when the needle is not in the port, the need to position an external unit on top of the medical device during refill (perhaps in sterile conditions), and uncertain electrical connections through the patient's tissue.

SUMMARY OF THE INVENTION

The present invention provides a detector integrated within an implantable port, such as the refill port of an implantable drug delivery device, for detecting the proper placement of a needle in the port. The detector can activate a predefined function of the implantable drug delivery device such as an alarm and/or a predefined diagnostic function.

In a first aspect, the invention provides a refill port for an implantable device with integral refill instrument placement detection. The refill port includes a pierceable septum and a detector. The pierceable septum is disposed on the refill port for admitting a refill instrument has a first outer surface at least a portion of which is exposed outside the refill port and a second inner surface at least a portion of which is exposed inside the refill port. The detector is disposed inside the refill port with respect to the second inner surface of the pierceable septum for determining the placement of a refill instrument within the refill port.

In another aspect, the invention provides, in a refillable, implantable, drug delivery pump having a drug chamber and control electronics, a refill port having a pierceable septum and a detector. The pierceable septum is disposed on the refill port for admitting a refill instrument has a first outer surface at least a portion of which is exposed outside the refill port and a second inner surface at least a portion of which is exposed inside the refill port. The detector is disposed inside the refill port with respect to the second inner surface of the pierceable septum for determining the placement of a refill instrument within the refill port and generating an electronic communication in response to the placement. The detector is electrically connected to the control electronics to trigger a refill diagnostic procedure based upon a refill instrument placement communication from the detector to the control electronics.

In a further aspect, the invention provides a refillable, implantable, drug delivery pump having a drug chamber, control electronics, and a refill port. The refill port includes a refill port base, a pierceable septum, and a detector. The refill port base defines a refill port chamber and a fluidic channel between the refill port chamber and the drug chamber. The pierceable septum is disposed proximate a first end of the refill port chamber for admitting a refill needle. The pierceable septum also has a first outer surface at least a portion of which is exposed outside the refill port chamber and a second inner surface at least a portion of which is exposed inside the refill port chamber. The detector is disposed within the refill port for determining the placement of a refill needle within the refill port chamber and generating an electronic communication in response to the placement. The detector includes a first movable detector element disposed within the refill port chamber for moving in response to contact from a refill needle and a second detector element fluidically separated from the refill port chamber and configured to detect movement by the first movable detector element indicating contact from a refill needle. The detector is further electrically connected to the control electronics to trigger a refill diagnostic procedure based upon a refill needle placement communication from the detector to the control electronics.

In a further aspect, the invention includes a method for detecting the placement of a refill instrument within a refill port in an implantable drug delivery pump having a drug chamber and control electronics. The method includes providing a refill port having a detector for determining the placement of a refill instrument within the refill port. The detector communicates to the control electronics based upon the placement of a refill instrument within the refill port and the control electronics signals an alarm to indicate the the placement of a refill instrument within the refill port.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides a detector integrated within an implantable port, such as the refill port of an implantable drug delivery pump. The detector can detect the proper placement of a refill instrument, such as a needle and syringe, within the port for refilling the pump. The detector can be connected to control electronics within the pump and can activate a predefined function of the implantable drug delivery pump, such as an alarm and/or a predefined diagnostic function, upon either placement of the refill instrument within the port or removal of the refill instrument from the port.

Implantable drug delivery pumps are typically implanted one inch beneath the patient's skin in the lower abdomen or upper chest. Suture loops on the outer casing of the pump attach the pump in place. Pump implantation is done in the operating room with the patient under local or general anesthesia. The surgery is typically completed within one to three hours, and patients usually have a 24 hour or less hospital stay. For patients who are treated with implantable drug delivery pumps for intractable chronic pain, the pumps may remain in place for many years.

Implantable drug delivery pumps are typically made of a biocompatible metal (e.g., titanium) and are approximately two to three inches wide, three quarters to one inch deep and weigh up to six ounces. The pump can be constant flow or programmable, with either having a reservoir to store the drug to be delivered. Reservoir volume typically varies between 18 to 60 ml. Depending upon the volume of the reservoir and the flow rate, chronic pain patients may need a refill of morphine every one to two months. Thus, many pumps include a small raised port having a rubber septum that is periodically accessed with a special needle through the skin to refill the pump's drug storage reservoir.

Figure 1:
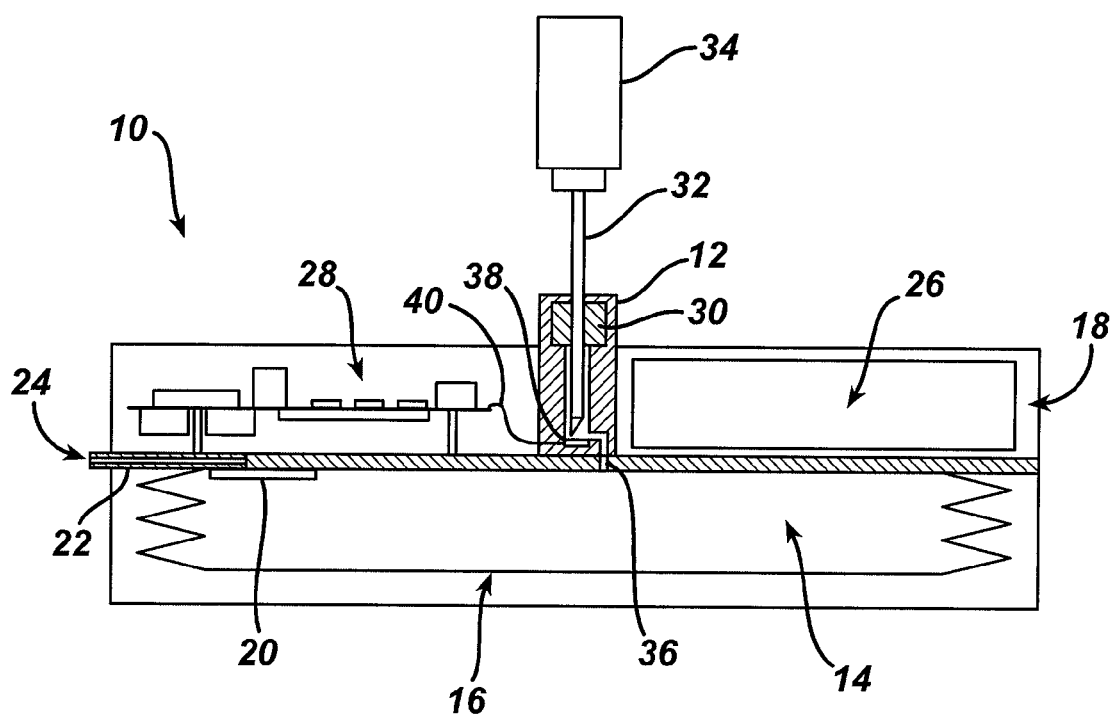
FIG. 1 is a cross-sectional view of a refillable, implantable drug delivery pump of the invention.

One embodiment of a refill port 12 of the invention provided on an implantable drug delivery pump 10 is illustrated in FIG. 1. Pump 10 generally includes three hermetically sealed chambers: a drug chamber 14, a pressurized gas chamber 16, and an electronics chamber 18. Drug chamber 14 provides a reservoir for the drug that is delivered by the pump to the patient. In pump 10, drug chamber 14 is a flexible bellows that is pressured from the outside by pressurized gas in pressurized gas chamber 16. A capillary chip and filter 20 releases a constant flow of drug from drug chamber 14 into fluidic connection channel 22 toward pump outlet 24.

Electronics chamber 18 houses a battery 26 and control electronics 28. As will be further explained below, control electronics 28 can control the flow of drug from fluidic connection channel 22 to pump outlet 24, communicate with an external controller or programmer, and perform a number of self-test diagnostics on pump 10.

Refill port 12 includes a refill septum 30 for admitting a drug refill instrument such as needle 32 connected to syringe 34 which will contain a refill amount of drug to be provided to drug chamber 14 through fluidic connection channel 36. Inside refill port 12, a detector such as detection switch 38 is provided to generate an electronic communication on connections wires 40 to control electronics 28 upon detection of the placement of needle 32 within the refill port. Based on this communication, control electronics 28 can generate an alarm to indicate to the person placing the needle that it has been appropriately placed and/or run diagnostic tests.

Figure 2:
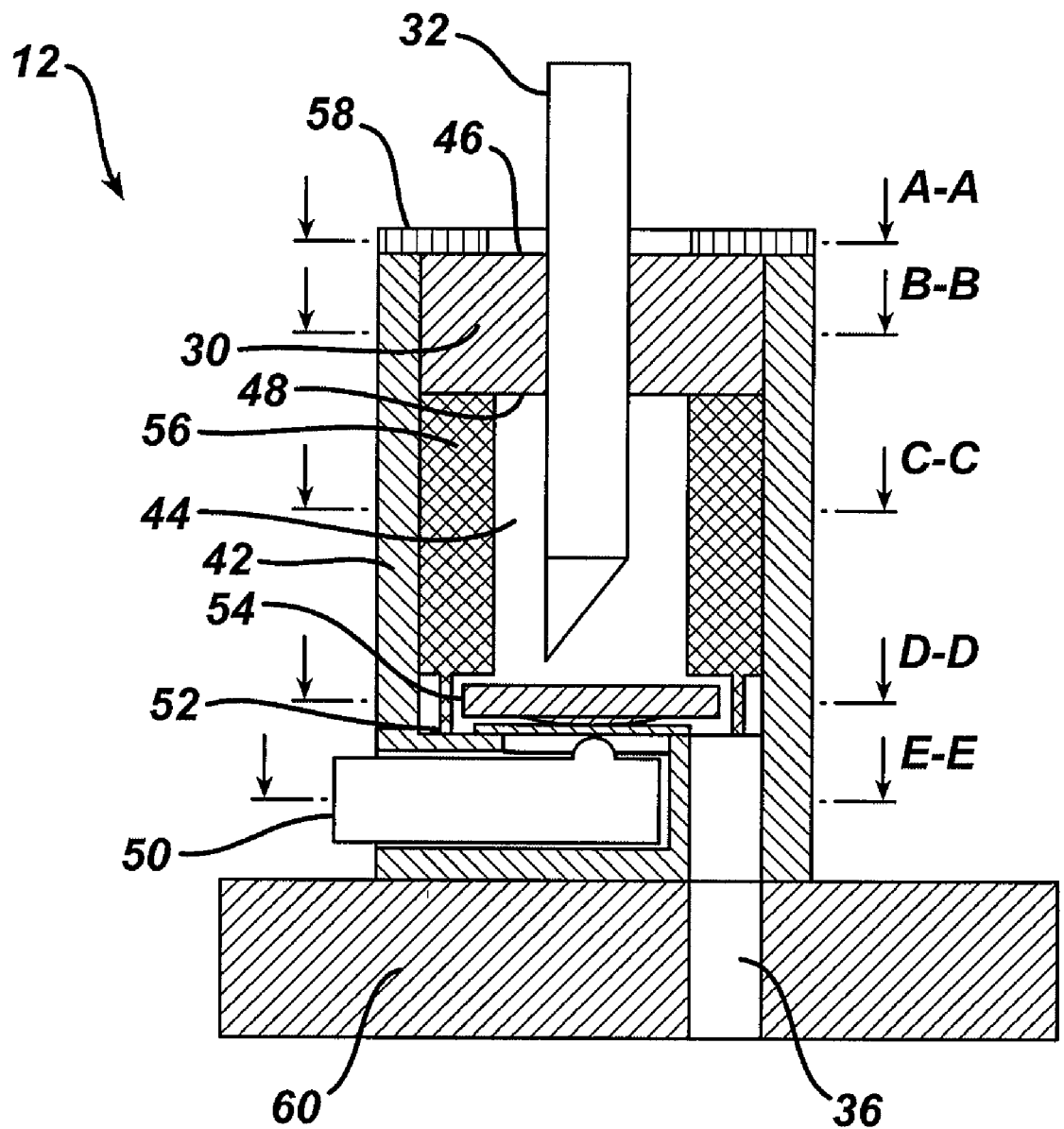
FIG. 2 is a cross-sectional view of a refill port of the pump of FIG. 1.
Figure 2A:
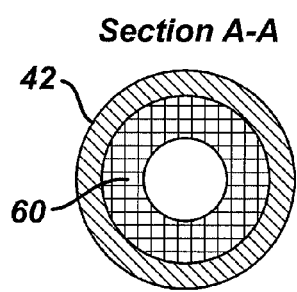
FIGS. 2A through 2E are cross-sectional views of the refill port of FIG. 2 taken along lines A-A through E-E, respectively.
Figure 2B:
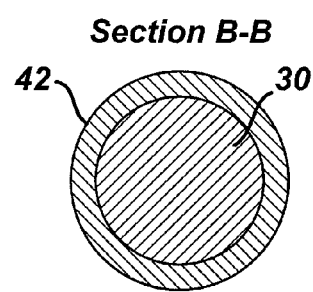
Figure 2C:
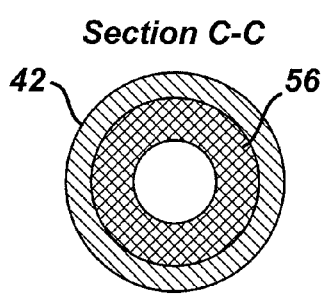
Figure 2D:
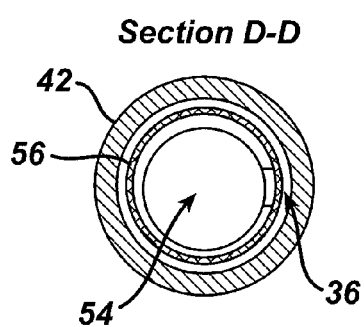
Figure 2E:
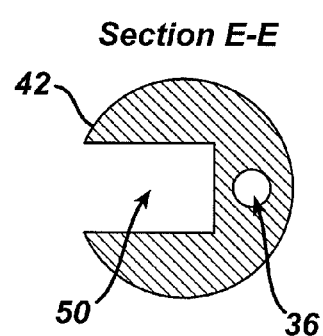

Further details of refill port 12 are illustrated in FIG. 2, as well as in the cross-sectional views of refill port 12 provided in FIGS. 2A through 2E. Refill port base 42, along with refill septum 30 disposed on a first end of the base, generally define a refill port chamber 44. Refill septum 30 includes a first outer surface 46 that is at least partially exposed outside the refill port where it can be penetrated by needle 32. Refill septum 30 also includes a second inner surface 48 that generally defines an inner boundary of the refill port chamber; once needle 32 passes the second inner surface, particularly so that a dispensing orifice of the needle completely passes the second inner surface, the needle is within the refill port for refilling purposes.

In the illustrated embodiment, detector 38 includes switch 50, membrane 52, and needle plate 54. Membrane 52 is resilient so that it can move in response to placement of needle 32 so as to activate switch 50. In one embodiment, refill port base 42 can be made of titanium or a titanium alloy and membrane 52, which can be made of the same material, is thin enough to allow it to flex and can be laser welded to the refill port base to create a fluid tight seal. Switch 30, which is on the opposite side of membrane 52 from refill port chamber 44, can thus be separated from the drug. Needle plate 54 can also be provided to contact needle 32 upon its entry and advance to the plate and translate that contact into movement of membrane 52 to activate switch 50. Needle plate 54 can be made of a tough plastic material so that it can withstand multiple needle contacts. While not strictly necessary to translate the motion of needle 32 to switch 50, where, as in this embodiment, membrane 52 is made thin (on the order of 100 microns for titanium) so as to be movable, needle plate 54 provides protection for membrane 52 against damage from contacting the needle and can thereby increase the reliability of the system.

A centering ring 56 can also be disposed inside refill port base 42 to help center needle plate 54 within the refill port and also to guide needle 32 to the needle plate. This configuration places needle plate 54 at a second end of refill port chamber 44 with respect to refill septum 30. Accordingly, needle 32 must be fully advanced into the refill port in order to trigger switch 50. While this degree of advancement is not necessary to the invention, it provides an extra measure of safety by ensuring that the needle is fully and deeply placed within the refill port. Further, centering ring 56 is configured to allow fluid to flow past needle plate 54 to fluidic connection channel 36 so as to maintain a fluidic connection between refill port chamber 44 and drug chamber 14 for this configuration.

Refill septum 30 can be forced within refill port base 42 on top of centering ring 56 and locked into place by closing ring 58. Refill septum 30 can be a self sealing septum as is known in the art and can, for example, be made of a silicone material. Refill port base 42 can be attached to baseplate 60, which can be a border between electronics chamber 18 and drug chamber 14, and the base and baseplate together can define fluidic connection channel 36 between refill port chamber 44 and drug chamber 14.

FIG. 2 illustrates a detector that comprises a microelectromechanical switch located at the bottom of the refill port chamber. This configuration is convenient in that it can be readily manufactured and allows the use of a standard microelectromechanical switch, however, a person of ordinary skill in the art will recognize that other detectors and configurations are possible within the scope of the invention, including, for example, electromechanical switches of other configurations, electrical switches closed by contact with the refill needle, and optical detectors. While locating the detector so that the needle placement is detected only when the needle is fully inserted into the port has advantages, the detector need only detect that the needle is inside the refill port chamber with respect to the septum, and preferably when the drug dispensing orifice of the needle is fully within the refill port chamber with respect to the septum.

In addition, the electronic communication communicated by the detector to the control electronics can be as simple as an open or closed indication. For example, a voltage can be applied to switch 50 on one connection wire 40 with the switch being in an open condition. Needle 32 can then trigger switch 50 to a closed position so that the voltage appears on a second connection wire 50 to signal to control electronics 28 that the needle has been properly placed. In this manner, the detector is a passive element and only draws current (based on a typically small resistance through the switch circuit) when the needle triggers switch 50, advantageously resulting in low power consumption by the detector as compared to other approaches.

As noted above, the drug to be delivered is pressurized by pressurized gas chamber 16 and flows into the patient through capillary chip and filter 20, fluidic connection channel 22, and pump outlet 24, which is typically connected to a delivery catheter. Pressurized gas chamber 16 can contain a chemically inert liquid gas mixture which acts as a propellant. Drug chamber 14 can be configured as a titanium bellow upon which the gas propellant exerts a constant pressure to press the drug through a filter and throttle passage (capillary chip and filter 20) to pump outlet 24.

Figure 3:
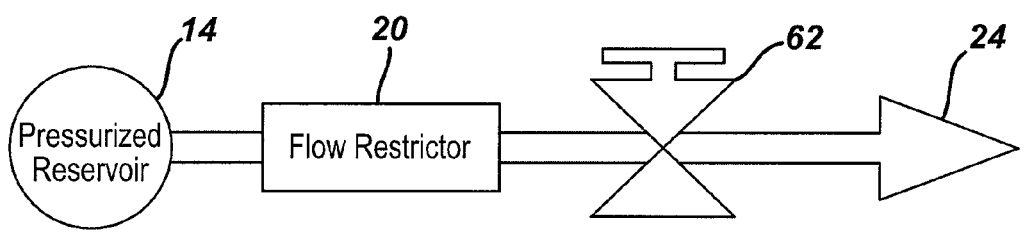
FIG. 3 is a diagram illustrating the flow of a drug through the pump of FIG. 1.

As further illustrated in FIG. 3, a microvalve 62 that controls the flow rate of the infusion pump can be provided at the end of the restrictor chip 20. Microvalve 62, which can be part of or connected to control electronics 28, opens and closes once within a set period of time so that the time of the open position together with the flow rate of the restrictor chip determines the flow rate of the infusion pump. By changing the duty cycle of the valve (ratio of open to closed state), the flow rate can be adjusted between 0 ml/day (valve always closed) and the maximum flow rate given by the flow restrictor (valve always open). Control electronics 28 can monitor and test this flow rate by polling a drug level sensor at a regular time interval, say once every 24 hours, and comparing each polling result to the previous result to determine whether the flow rate over time conforms to the intended flow rate.

Figure 4:
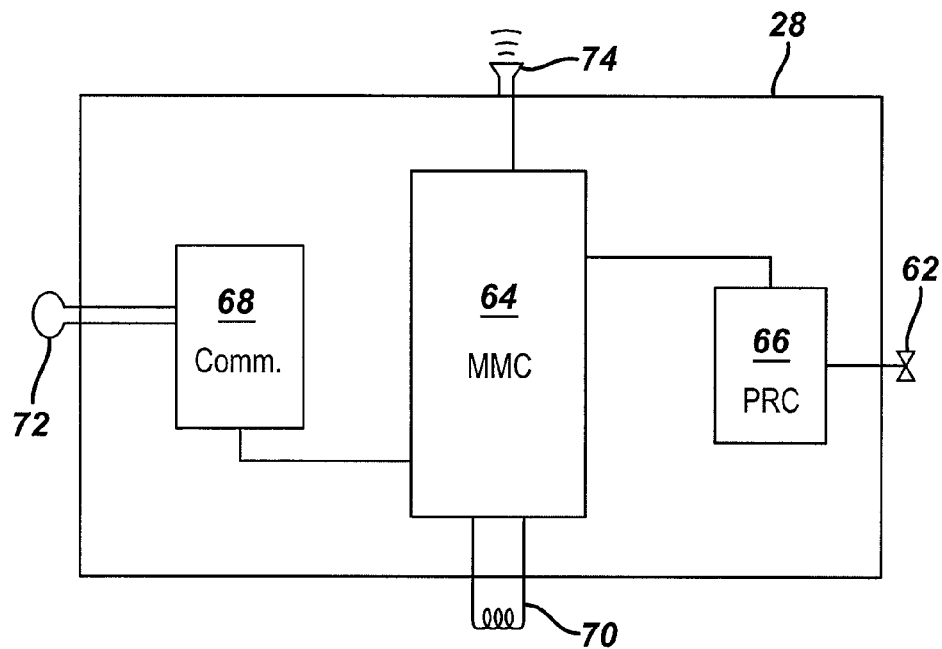
FIG. 4 is a diagram illustrating certain functionality of control electronics of the pump of FIG. 1.

The further operation of control electronics 28 can be explained by reference to the functional block diagram of FIG. 4. Control electronics 28 can have a main micro controller block 64 that handles all housekeeping functions and management and communications functions within the control electronics. Prescription rate controller block 66 can handle real time control of microvalve 62 including setting the drug flow rate and regulating the supply of power to the valve. A communications block 68 manages communications with an external controller or programmer and may also manage radio frequency energy delivery from the external controller through antenna 72. All or various ones of these functions could be integrated within a single controller, however, spreading the functions among separate hardware elements allows for the elements to be powered up only when needed, thus reducing overall energy requirements for the pump.

Control electronics 28 also includes a self-test or diagnostic capability. In particular, control electronics 28 includes a drug level sensor 70 capable of determining the amount of medication remaining in drug chamber 14. As part of a regularly scheduled self-test routine, every 24 hours for example, the drug level can be measured and compared to a previously stored drug level value to check whether the flow rate of drug from the pump matches the desired profile. In addition, when the drug level reaches a low level amount, control electronics can set an alarm, such as buzzer 74, so that the patient and/or doctor is aware of the need to refill the drug reservoir. In addition, control electronics 28 can include a diagnostic test of drug level sensor's integrity to indicate whether the sensor is functioning properly.

Control electronics 28 can also include a number of self-test routines such as microvalve 62 operational checks, memory checks, temperature checks, battery checks, crystal frequency checks, and other self-test features as are known in the art. Control electronics 28 can also include a pressure sensor for sensing the pressure of the drug in drug chamber 14 and/or refill port chamber 44.

Having such features, when control electronics 28 receives a signal from detector 38 that a needle has been placed in the refill port, it can trigger a number of diagnostic features. One such feature would be to begin continuous or short interval sensing of the drug pressure. In this way, if pressures during refill should exceed some threshold level, an alarm could alert the user to reduce pressure on the syringe before a high pressure condition damages drug chamber 14 or other parts of the pump. As pump 10 of FIGS. 1 and 2 has no check valve or other pressure differential feature between drug chamber 14 and refill port chamber 44, pressure sensing could be performed in either chamber.

Another such feature would be to test the integrity of drug level sensor 70 and test the drug level upon placement of needle 32 within refill port chamber 44 and test the drug level again upon removal of the needle from the refill port chamber. In this way, control electronics 28 could track the amount of drug added during the refill. Having monitored the amount of drug added during the refill in this manner, control electronics 28 could either not perform a drug flow test (as described above) at the next scheduled interval, or it could take the amount of the refill into account when comparing the tested drug level to the previous test level. In exemplary pump 10, this testing would rely upon the doctor to maintain some pressure on needle 32 while it is in refill port chamber 44 in order to maintain switch 50 in a depressed state until removal of the needle. In general, it is expected that a doctor would maintain such pressure on needle 32 in order to insure that the needle does not unintentionally leave refill port chamber 44. However, the diagnostic program could be configured to account even for intermittent switch contact during a refill procedure.

An alternative method for performing this testing would be to test the integrity of drug level sensor 70 and begin continuous or short interval drug level tests upon placement of needle 32 within refill port chamber 44. Control electronics 28 could then track the amount added until it reaches a high drug level amount, and issue another alarm to alert the user that the pump has been filled to a certain level. Alternatively, control electronics 28 could measure the drug level until the drug level stopped rising over a given period of time. Again, based on this data, control electronics 28 could either not perform a drug flow test (as described above) at the next scheduled interval, or it could take the amount of the refill into account when comparing the tested drug level to the previous test level.

Alternatively or in addition to tracking the refilling of the pump, control electronics 28 can run any other self test function or can run a complete self test, either upon placement of the needle in the refill port or upon completion of the refill as indicated either by the drug level sensor testing or by an indication from detector 38 that the needle has been removed from its position. In particular, upon completion of the refill, control electronics 28 could perform a valve operation test to insure that microvalve 62 was operating properly following the refill.

The invention, including both systems and methods, has been described with respect to the refillable, implantable infusion pump illustrated in FIGS. 1 and 2, however, a person of ordinary skill in the art will recognize that the invention can be applied to other refillable, implantable pumps as well. For example, the features of the invention can be added to implantable pumps such as the SynchroMed® line of implantable infusion pumps produced by Medtronic, Inc. of Minneapolis, Minn. or other pumps known in the art such as, for example, the implantable infusion pump provided in U.S. Pat. No. 6,740,075 to Lebel et al., which is hereby incorporated by reference. In addition, the detector of the present invention can trigger self test features of these pumps.

Accordingly, the embodiments of the present invention are not limited by what has been particularly shown and described, except as indicated by the appended claims. All publications and references cited herein are expressly incorporated herein by reference in their entirety.

What is claimed is:

1. A refill port for an implantable device with integral refill instrument placement detection, comprising:
   a pierceable septum disposed on the refill port for admitting a refill instrument, the pierceable septum having a first outer surface at least a portion of which is exposed outside the refill port and a second inner surface at least a portion of which is exposed inside the refill port;
   a detector disposed inside the refill port with respect to the second inner surface of the pierceable septum for determining the placement of a refill instrument within the refill port; and
   a base defining a refill port chamber for receiving a refill fluid;
   wherein the detector is a switch that is fluidically separated from the refill port chamber wherein a resilient membrane separates the switch from the refill port chamber while allowing movement from the placement of a refill instrument within the refill port chamber to be translated to the switch.

2. The refill port of claim 1, wherein the detector is a passive detector.

3. The refill port of claim 1, wherein the detector is configured to detect the placement of a refill instrument inside the refill port chamber.

4. The refill port of claim 3, wherein the detector is configured to detect the placement of a refill needle inside the refill port chamber.

5. The refill port of claim 4, wherein the detector is configured to detect the placement of a refill needle so that a dispensing orifice of the needle is inside the refill port chamber.

6. The refill port of claim 1, further comprising a needle plate disposed within the refill port chamber.

7. The refill port of claim 6, wherein the needle plate is configured to move in response to contact from the placement of a refill instrument within the refill port chamber so as to contact and move the resilient member to actuate the switch.

8. The refill port of claim 1, further comprising an implantable medical device integral with the refill port.

9. The refill port of claim 8, further comprising control electronics in communication with the detector, the detector sending an electronic communication to the control electronics based upon the placement of a refill instrument within the refill port.

10. The refill port of claim 9, wherein the electronic communication triggers an alarm to be signaled by the control electronics.

11. The refill port of claim 9, wherein the electronic communication triggers a diagnostic program to be run by the control electronics.

12. The refill port of claim 11, wherein the diagnostic program includes testing a fluid pressure.

13. The refill port of claim 11, wherein the diagnostic program includes testing a fluid level.

14. The system of claim 1, wherein the switch is a microelectromechanical switch.

15. In a refillable, implantable, drug delivery pump having a drug chamber and control electronics, a refill port system, comprising:
   a pierceable septum disposed on the refill port for admitting a refill instrument, the pierceable septum having a first outer surface at least a portion of which is exposed outside the refill port and a second inner surface at least a portion of which is exposed inside the refill port; and
   a detector disposed inside the refill port with respect to the second inner surface of the pierceable septum for determining the placement of a refill instrument within the refill port and generating an electronic communication in response to the placement;
   wherein the detector is electrically connected to the control electronics to trigger a refill diagnostic procedure based upon a refill instrument placement communication from the detector to the control electronics wherein a resilient membrane separates the switch from the refill port chamber while allowing movement from the placement of a refill instrument within the refill port chamber to be translated to the switch.

16. The system of claim 15, wherein the detector is a passive detector.

17. The system of claim 16, wherein the detector is a switch.

18. The system of claim 17, wherein the switch is a microelectromechanical switch.

19. The system of claim 15, wherein the refill port comprises a base defining a refill port chamber for receiving a refill fluid.

20. The system of claim 19, wherein the detector comprises a switch that is fluidically separated from the refill port chamber.

21. The system of claim 20, wherein the switch is a microelectromechanical switch.

22. The system of claim 15, further comprising a needle plate disposed within the refill port chamber.

23. The system of claim 22, wherein the needle plate is configured to move in response to contact from the placement of a refill instrument within the refill port chamber so as to contact and move the resilient member to actuate the switch.

24. The system of claim 15, wherein the refill instrument placement communication triggers a diagnostic procedure that includes testing a fluid pressure.

25. The system of claim 15, wherein the refill instrument placement communication triggers a diagnostic procedure that includes testing a fluid level.

26. A refillable, implantable, drug delivery pump system, comprising:
- a drug chamber;
- control electronics;
- a refill port including:
  - a refill port base defining a refill port chamber and defining a fluidic channel between the refill port chamber and the drug chamber;
  - a pierceable septum disposed proximate a first end of the refill port chamber for admitting a refill needle, the pierceable septum having a first outer surface at least a portion of which is exposed outside the refill port chamber and a second inner surface at least a portion of which is exposed inside the refill port chamber;
  - a detector disposed within the refill port for determining the placement of a refill needle within the refill port chamber and generating an electronic communication in response to the placement, the detector including:
    - a first movable detector element disposed within the refill port chamber for moving in response to contact from a refill needle; and
    - a second detector element comprising a switch fluidically separated by a resilient membrane from the refill port chamber and configured to detect movement by the first movable detector element indicating contact from a refill needle;
- wherein the detector is electrically connected to the control electronics to trigger at least one selected from the group consisting of an alarm and a refill diagnostic procedure based upon a refill needle placement communication from the detector to the control electronics.

27. The system of claim 26, wherein the refill instrument placement communication triggers a diagnostic procedure that includes testing a fluid pressure.

28. The system of claim 26, wherein the refill instrument placement communication triggers a diagnostic procedure that includes testing a fluid level.

* * * * *